(12) United States Patent
Bartels et al.

(10) Patent No.: US 7,617,004 B2
(45) Date of Patent: Nov. 10, 2009

(54) ELECTRODE LEAD

(75) Inventors: Klaus Bartels, Berlin (DE); Thomas Gunther, Wilhelmshorst (DE)

(73) Assignee: Biotronik CRM Patent AG, Baar (CH)

( * ) Notice: Subject to any disclaimer, the term of this patent is extended or adjusted under 35 U.S.C. 154(b) by 526 days.

(21) Appl. No.: 11/241,982

(22) Filed: Oct. 4, 2005

(65) Prior Publication Data

US 2006/0074470 A1   Apr. 6, 2006

(30) Foreign Application Priority Data

Oct. 4, 2004   (DE) ........................ 10 2004 048 991

(51) Int. Cl.
*A61N 1/05* (2006.01)
(52) U.S. Cl. ..................................... 607/116
(58) Field of Classification Search ................. 607/116, 607/117, 122
See application file for complete search history.

(56) References Cited

U.S. PATENT DOCUMENTS

| | | | | |
|---|---|---|---|---|
| 5,203,348 A | | 4/1993 | Dahl et al. | |
| 5,385,578 A | * | 1/1995 | Bush et al. | 607/122 |
| 5,755,762 A | * | 5/1998 | Bush | 607/122 |
| 6,129,752 A | * | 10/2000 | Neubauer et al. | 607/127 |
| 6,721,604 B1 | * | 4/2004 | Robinson et al. | 607/116 |
| 6,952,616 B2 | * | 10/2005 | Wessman et al. | 607/122 |
| 7,065,411 B2 | * | 6/2006 | Verness | 607/116 |

FOREIGN PATENT DOCUMENTS

EP   0680771 B1   11/2001

* cited by examiner

*Primary Examiner*—Carl H Layno
*Assistant Examiner*—Brian T Gedeon
(74) *Attorney, Agent, or Firm*—Browdy and Neimark, P.L.L.C.

(57) ABSTRACT

Implantable electrode lead for stimulation in or on the heart, comprising a body having an insulating and sealing outer surface, at least one electrical connection between an outwardly electrically active region having a connecting unit for the electrical connection to a cardiac pacemaker, cardioverter/defibrillator or other suitable electrically active implantable device, and an active or passive fixation. To reduce the electrical resistance while, at the same time, providing for a long life, the outwardly electrically active regions are manufactured with a component of high bioresistance, biocompatibility and non-toxicity, and a component with low electrical resistance.

16 Claims, 4 Drawing Sheets

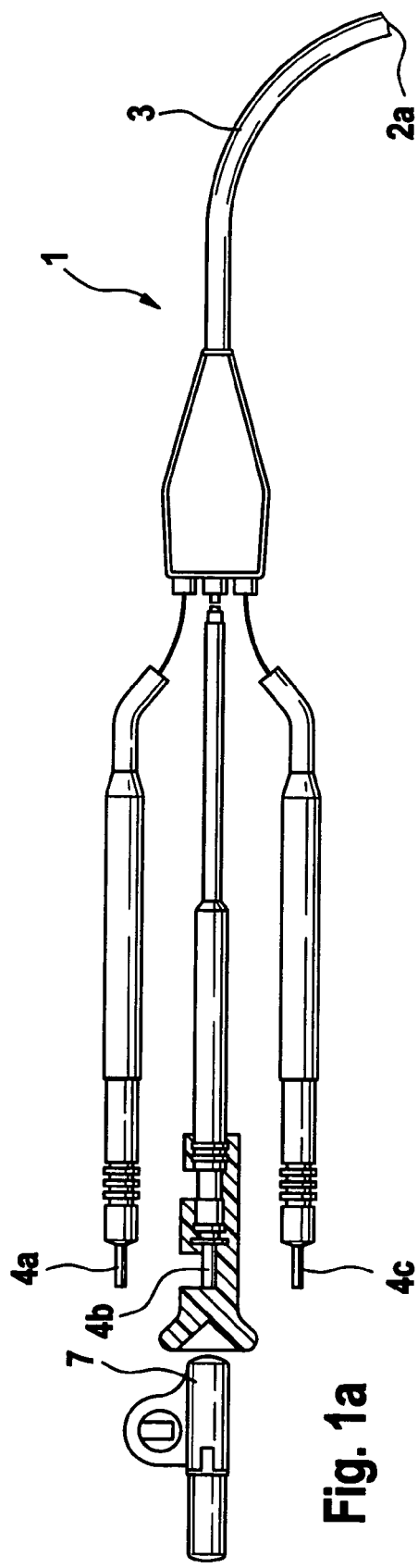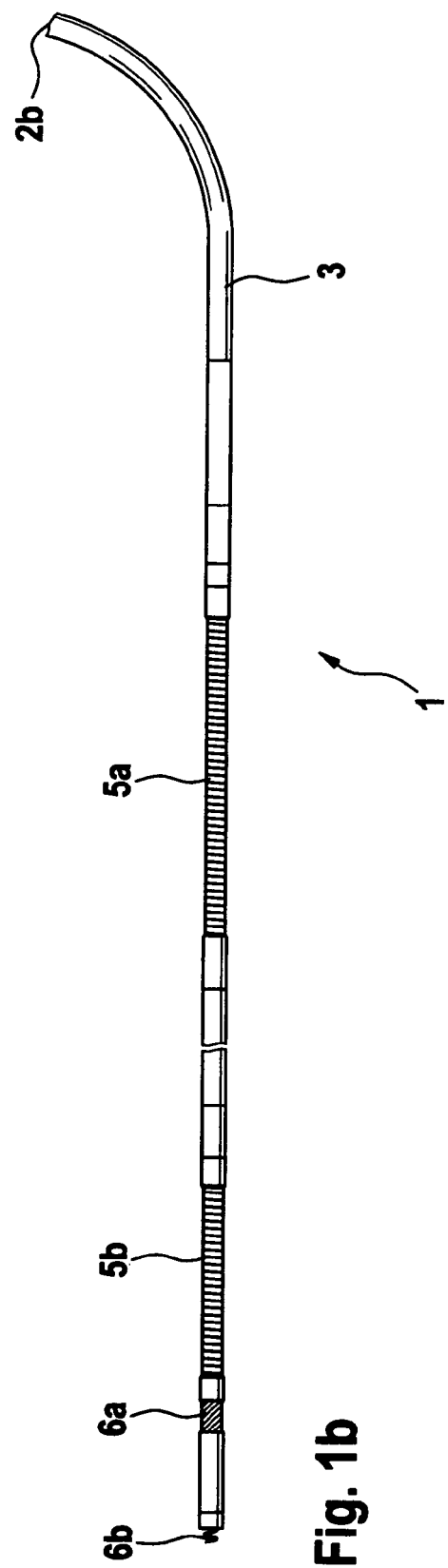

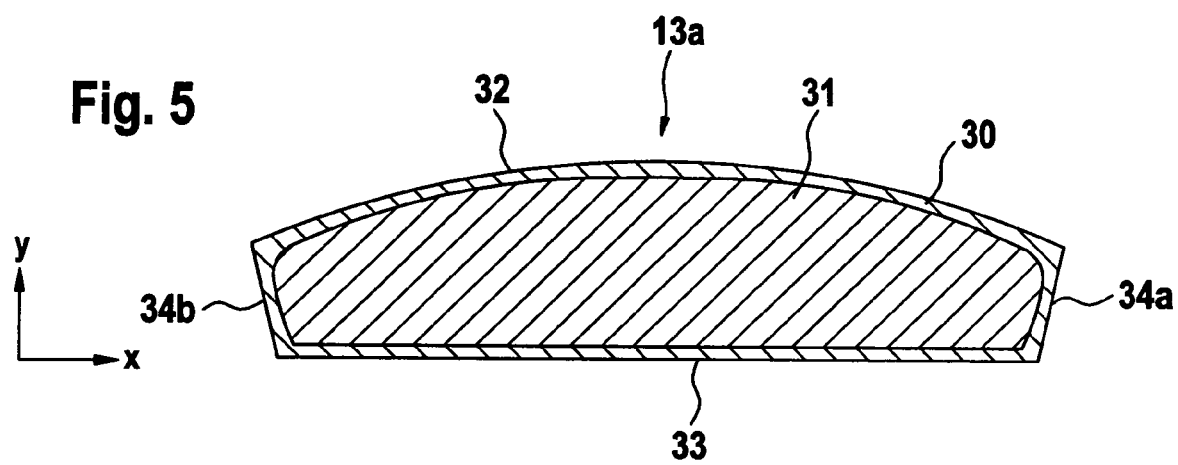

ELECTRODE LEAD

FIELD OF THE INVENTION

The invention relates to an implantable electrode lead, in particular a defibrillation electrode lead, comprising at least one electrical conductor having a proximal connection region for an electrotherapeutic implantable device as well as at least one electrically active outer surface that is connectable via the conductor to the electrotherapeutic implantable device.

BACKGROUND OF THE INVENTION

Electrode leads of the generic type are well known from the prior art. They serve as an electrical connection between an electrotherapeutic implantable device, which may be a neurostimulator, pacemaker, defibrillator or other suitable electrotherapeutic implantable device, and the location being treated in the body. These may be whole variety of locations in the body. One example given here is a cardiac electrode lead. The electrode leads not only serve to transmit therapeutic pulses, but they also serve to transmit body and measurement signals to the implant, so that an appropriate treatment can take place specifically in response to the body signals. This treatment may represent a stimulation pulse that is suitable for replacing the missing stimulus generation. The treatment may also be a high-energy defibrillation pulse.

In medical technology the term electrode lead is referred to in short, as "electrode". It refers in this definition not only to the point of transition of the electric energy according to the physical definition, but it also refers to the line consisting of the electrical conductor including its enveloping insulation, as well as to all other functional elements that are permanently connected to the line. For reasons of clarity, the section of the electrode that actually functions within the physical meaning, which includes the point of transition of the electric energy, will be referred to below as "electrically active region".

Measures must be taken to ensure that a long-term implantation in the body—i.e., in a highly corrosive environment—occurs without significant degradation processes and does not result in an undesirable immunological reaction.

For the region of the long stretched-out feed line, which must, of course, be electrically insulated toward the outside, biocompatible synthetic materials present themselves. The most important synthetic material in this context is silicone rubber.

For the region of the electrically active region it is important to take into consideration electrophysical effects. An electrically active region of an implantable electrode must have a low electrical resistance. This is decisive for a successful emittance of stimulation pulses, since an implantable medical device is dependent upon an independent power supply. This power supply is ensured by means of a battery, which, obviously, has a limited size.

To be avoided is the formation of a corrosion layer, which causes the electrical resistance to increase, with the consequence that endogenous signals can not be transmitted correctly to the implantable medical device. Also, the energy output increases as well.

Regarded as commonly used material with high bioresistance, but also with high electrical resistance, are cobalt-chrome alloys (e.g. MP35N). Platinum, iridium, or an alloy of these two metals are also regarded as bioresistant materials. The platinum-iridium alloys, in particular, are known for having a high electrical resistance.

SUMMARY OF THE INVENTION

It is the object of the invention to make available an implantable electrode lead that incorporates least one electrically active region for the electrical stimulation of cardiac tissue and avoids the above-mentioned shortcomings. This object is met according to the invention with the outwardly electrically active region being composed of at least one element of "Drawn Filled Tube" (DFT) having
- a component of high bioresistance, biocompatibility and non-toxicity, and
- a component with low electrical resistance.

The inventive electrode has a long stretched-out body having a proximal and a distal end. Provided at the proximal end is a connection to an electrotherapeutic implantable device. This device may be a pacemaker, cardioverter/defibrillator or other suitable heart rhythm device. Disposed at the distal end is a fastening means for the secure fastening of the electrode to the cardiac tissue. This may be a so-called passive fixation on one hand, which is designed anchor-shaped and in this manner can interlock with the trabecules of the ventricular heart muscle. One example for an electrode of this type can be seen in U.S. Pat. No. 6,236,893 B1. On the other hand, it may be an active fixation that can be actively screwed into the cardiac tissue by means of a screwable helix-shaped screw. This screw electrode may be electrically conductive as well, and thus act as an additional electrically active region. An active fixation of this type is described, for example, in EP 0 680 771. The medial region of the electrode, which is located between the proximal and distal end, is sealed against the environment and insulated. The outer surface is coated in this case with silicone or similar synthetic material. In the distal region of this electrode, the sealed and insulated outer surface is interrupted by at least one electrically active region. These electrically active regions are additional electrodes that may, for example, permit a stimulation of the above type in the atrium of the heart. Said areas may also be designed floating, i.e., the electrically active regions are not located at the wall but "swim" along in the bloodstream.

All electrically active regions have at least one element made of DFT (Drawn Filled Tube) consisting of two components, namely a bioresistant, biocompatible and non-toxic component, and a component made of a material with low electrical resistance. The one component is usually designed such as to protect the other component. A bioresistant, biocompatible and non-toxic component protects another component made of a material with low electrical resistance. Preferred are platinum, iridium, or an alloy of these two materials.

According to the invention, the special electrophysical properties of an electrically active region are:
- Low electrical resistance and
- High bioresistance to corrosion.

These two properties do not exist in any known material up to now. Materials with low electrical resistance usually have a low bioresistance, and vice versa. According to the invention, this problem is solved with a thin layer of bioresistant material and high electrical resistance on a core of a material with low electrical resistance. If the material with the high electrical resistance is appropriately dimensioned, the total resistance of the system of both components is altered only insignificantly.

In one embodiment the core with the low electrical resistance is composed of a material from the vanadium group ($5^{th}$ subgroup of the classification of elements) or copper group ($1^{st}$ subgroup of the classification of elements). The core of the DFT wire is preferably composed of tantalum (Ta), niobium (Nb) or gold (Au).

The invention will be explained below based on a defibrillation electrode. The electrode may also be a cardiac electrode of a different type, such as an intracardial or epicardial pacemaker electrode.

BRIEF DESCRIPTION OF THE DRAWINGS

FIG. 1a shows a partial view of the proximal region of the electrode,

FIG. 1b shows a partial view of the distal region of the electrode,

FIG. 5 shows a section through an element of the shock coil.

DESCRIPTION OF THE PREFERRED EMBODIMENTS

Figure 2:
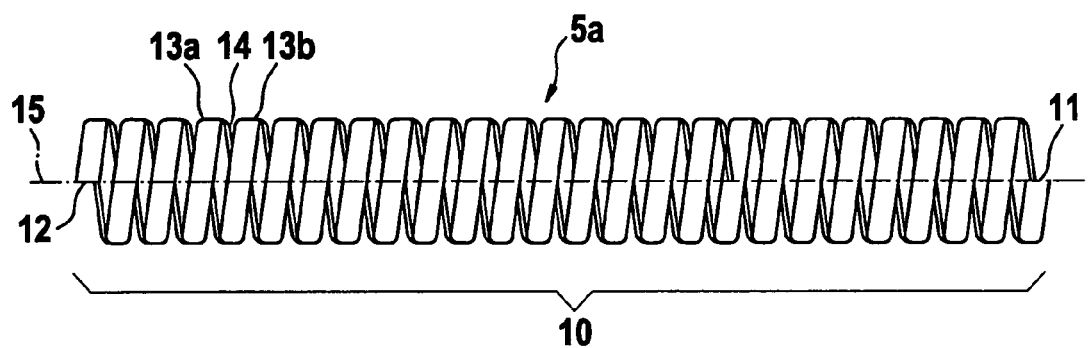
FIG. 2 shows a detail view of a shock coil of a defibrillation electrode.

FIG. 1a shows the proximal region of a defibrillation electrode lead 1 having an electrode body 3 that is electrically insulated and sealed toward the outside, various proximal connectors 4a, 4b, and 4c for the electrical contact with an electrotherapeutic implantable device not visible here, and a partially visible guide wire 7, which ensures a reliable feeding of the electrode into the region of the heart being treated. The guide wire 7 is removed after the electrode has been successfully implanted.

FIG. 1b additionally shows the distal region of the defibrillation electrode lead 1 with an outwardly insulated and sealed electrode body 3 representing the electrically and therapeutically active region of the electrode. Shown are the different electrically active regions embedded in the electrode body 3, like under 5a and 5b two independent shock coils for delivering a therapeutic high-energy pulse to the cardiac tissue, and the two measuring electrodes 6a and 6b, which permit an intracardial measurement of biosignals. The measured signals permitting a targeted treatment by means of the two shock coils 5a and 5b.

In FIG. 1b the distal region of a so-called actively fixable electrode is shown. This means that the electrode must be connected to the cardiac tissue by means of an element that is actuated by the user. This is accomplished with a type of screw that is situated at the distal end. One advantage of this design is the utilization as an electrically active region. The measuring electrode 6b is, at the same time, the active fixation. The mechanism is shown more clearly in FIG. 4. It depicts the distal end of the defibrillation electrode 1 with a portion of the electrically insulated and sealed electrode body 3 and portions of the electrically active regions embedded therein, which are the shock coil 5b and the measuring electrodes 6a and 6b. Clearly visible is the helix-shaped active fixation, which is rotatable relative to the electrode body 3 and can, therefore, be screwed into the heart.

In an additional embodiment of this invention a passive fixation will be described which—as can be inferred from the name—does not need to be actively attached to the cardiac tissue by the user. The passive interlocking connection is designed anchor-shaped in such a way that the electrode automatically interlocks itself with the trabecules of the cardiac tissue.

The proximal region (FIG. 1a) and the distal region (FIG. 1b) are connected to one another at the respective ends 2a and 2b. Between 2a in FIG. 1a and 2b in FIG. 1b there may be length that is not defined in detail, which is design-related.

FIG. 2 is a detail view of the shock coil 4a or 4b of a defibrillation electrode 1 having a proximal end 11 and a distal end 12. Between the two ends 11 and 12 the shock coil is wound helically. In order to attain a better flexibility and better embedding in the electrically insulating and sealing electrode body 3, the coil is wound in such a way that a clearance 14 is provided between two windings 13a and 13b. If the coil is wound transversal to the axis 15, the clearance 14 is reduced on the inside of the winding, on the outside the clearance 14 increases.

In a preferred embodiment the coil is implemented as a ribbon whose dimension is longer in the axial than in the radial direction. The larger contact area of the electrically active helixes with the cardiac tissue that is obtained in this manner offers advantages in the transmission of the high-energy pulse to the cardiac tissue.

In another embodiment the shock coil is formed of a round wire.

Figure 3:
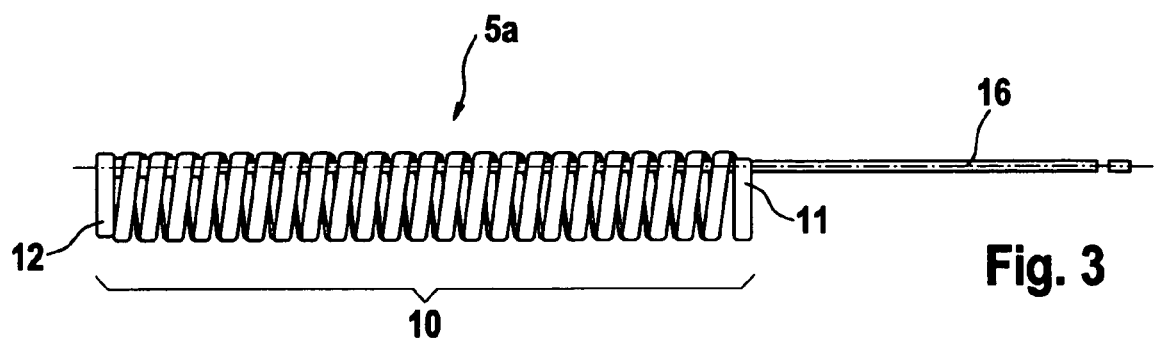
FIG. 3 shows a detail view of a shock coil of a defibrillation electrode with an electrical feed line.

FIG. 3 shows the above described shock coils 4a or 4b of a defibrillation electrode 1 having a proximal end 11 and a distal end 13 with an electrically conductive connection 16 extending inside the outwardly electrically insulating and sealing electrode body 12, and an electrical connection to one of the connecting units 4a, 4b or 4c that are provided for the connection to an electrically active implantable device. The electrically conductive connection is permanently connected to the shock coil 10 at the proximal and distal ends 11 and 12 by means of thermal connecting methods, such as welding or soldering, in order to thus create a reliable electrical connection. The electrically conductive connection is preferably a DFT cable, as described in EP 0 927 561 B1. In additional, different embodiments it may also be a wire, a DFT wire, an electrically conductive ribbon, an electrically conductive DFT ribbon, or an electrically conductive synthetic material.

Figure 4:
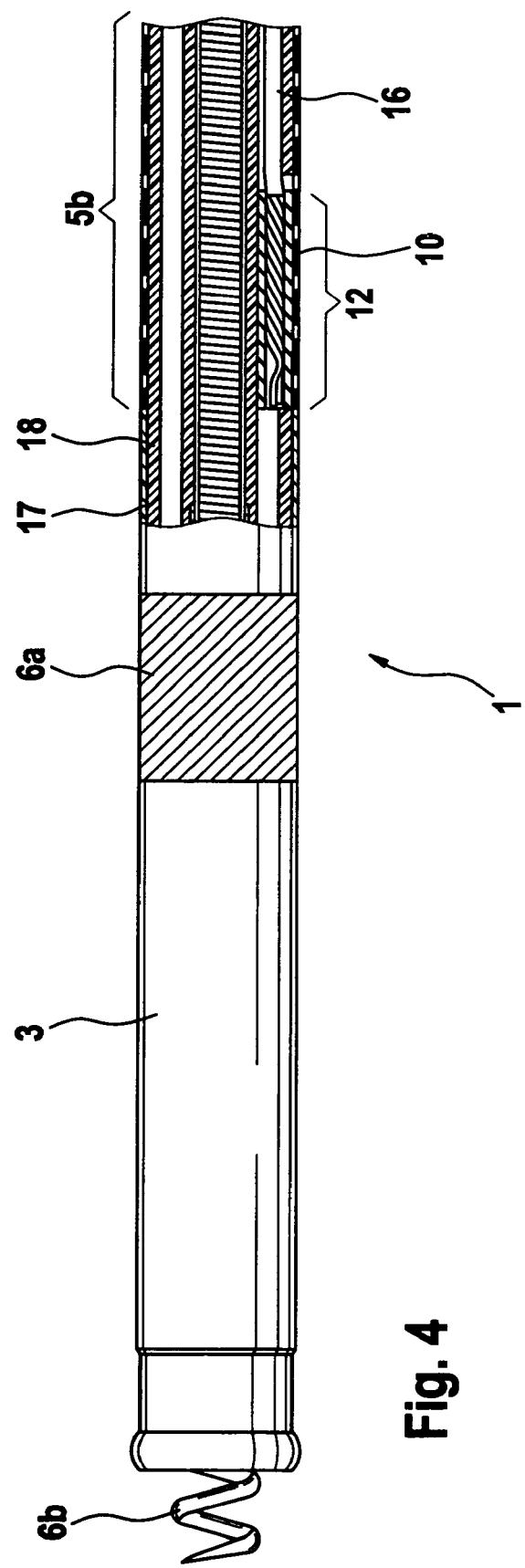
FIG. 4 shows a partial section through the distal region of the defibrillation electrode.

FIG. 4 shows a partial section through the distal region of the defibrillation electrode with an outwardly electrically insulating and sealing electrode body 3, the electrically active regions 6a and 6b as measuring electrodes—the latter also used as active fixation in an actively fixable defibrillation electrode—and shock electrode 5b for delivering high-energy pulses to the cardiac tissue. The electrode body is composed of an outer synthetic-material layer 17 and an additional synthetic-material layer 18 radially inwardly adjoining the outer synthetic-material layer.

Additionally located in the electrode body 3 are one or multiple electrically conductive connections 16 and a lumen 19 for receiving the guide wire during implantation of the electrode in the heart.

The outer synthetic-material layer 17 ensures the electrical insulation and fluid seal. Additionally, the material of the layer is selected such that it reduces the friction between the vessel wall and electrode so as to permit an easy insertion of the electrode through the vessel system to the heart. The outer synthetic-material layer 17 is formed of a biostable synthetic material. This is preferably a silicone rubber. The inner synthetic-material layer mainly serves to hold the shape of the electrode and to absorb influences in the form of inwardly directed forces. This layer is also formed of a biocompatible synthetic material. This is preferably a polyurethane. Additionally, biocompatible synthetic materials on the basis of polycarbonates, epoxysilane, polysulfone, polyethylene, and polyester also present themselves for both layers 17 and 18.

Also visible in FIG. 4 is that the electrically active region 5b—like the electrically active region 5a and 6a—is embedded in the outer synthetic-material layer 17. This ensures a friction-free implantation of the electrode. At the distal end 12 the electrically active region 5b is permanently connected to an electrically conductive connection 16.

FIG. 5 shows a section through a winding 13a or 13b of the electrically active region 5a or 5b. Visible is a DFT ribbon of an additional embodiment. It consists of an enveloping component 30 and a core component 31. An additional embodiment of the invention is a DFT wire with a concentric design of the enveloping component 30 and core component 31.

The enveloping component 30 of a material with high bioresistance and high electrical resistance is composed of platinum, iridium, or an alloy of the two materials. The core component 31 of a material with low electrical resistance but relatively low bioresistance is preferably from the vanadium group ($5^{th}$ subgroup of the classification of elements) or copper group ($1^{st}$ subgroup of the classification of elements). The core component 31 preferably consists of tantalum, niobium or gold. The thickness ratio between the enveloping component 30 and core component 31 is 1:3 to 1:40. If the electrically active region has a coil from a ribbon, then the thickness ratio between the enveloping component 30 and core component 31 is between 1:20 and 1:40 in the x-direction, and between 1:2 and 1:10 in the y-direction, particularly advantageous is a ratio in the x-direction between 1:25 and 1:30 and in the y-direction between 1:3 and 1:8. Particularly suitable, however, is a ratio in the x-direction between 1:27 and 1:29 and in the y-direction between 1:4 and 1:7.

The outer contour of the enveloping component 30 of the shown section through a helix 13a or 13b is designed in an advantageous manner and consists of three components:

a base 33 essentially facing in the inwardly oriented side of the electrode body 3, two opposed sides 34a and 34b, facing in the direction of the distal or proximal end of the electrically active regions 5a, 5b, or 6a, and a half-round configuration 32 consisting of the segment of a circle facing in the outwardly oriented side of the electrode body.

The base 33 lies on the inside outer layer 18 of the electrode body 3 and is constructed of a straight section in the x-direction. The two sides 34a and 34b are completely embedded in the outer layer 17. They extend away in the xy-coordinate system from the base 33 with a comparatively larger y-component than x-component. The side 34a faces, with an identical y-component having an opposed identical x-component, toward side 34b, away from the base 33. The half-round configuration 32 has a radius about a virtual center point that is many times longer than half the diameter of the electrode body 3. The summit of the half-round configuration 32 therefore projects out from the electrode body 3. This advantageous design has advantages in the transmission of a pulse to the cardiac tissue especially at the boundary areas between the electrically active regions and the electrically insulating and sealing electrode body 3.

The core component 31 in drawing 5a adapts to the outer contour of the enveloping component 30, however, it has rounded edges. The radius of the roundings of the core component 31 at the edges of the enveloping component 30 increases, the sharper the angle between the sides of the outer contour of the enveloping component 30.

What is claimed is:

1. An implantable electrode lead (1) for stimulation in or on the heart, comprising:

a long stretched-out electrode body (3) having a distal and a proximal end, at least one connecting unit (4a, 4b, 4c) for the electrical connection to an electrically active implantable device at the proximal end, a fixation device (6b) at the distal end, a largely electrically insulating and sealing outer surface (17) situated between the distal and proximal end, at least one electrically conductive connection (16) between the proximal and distal end, and at least one outwardly electrically active region (5a, 5b) in the distal region of the long stretched-out electrode body (3) that is electrically connected to one of the electrically conductive connections (16)

wherein:

the at least one outwardly electrically active region is composed of at least one element of "Drawn Filled Tube" (DFT) comprising an element of a helically wound DFT ribbon (13a), said element comprising:

an enveloping component (30) of high bioresistance, biocompatibility and non-toxicity, and a core component (31) with low electrical resistance, said core component (31) being a core of said element and said core component being enveloped by said enveloping component (30);

the DFT ribbon (13a) of the at least one electrically active region (5a, 5b) has in the distal region a radially outwardly oriented semi-circular surface (32); and the semi-circular surface (32) has a radius significantly larger than half the diameter of the electrode body (3).

2. An implantable electrode lead according to claim 1, wherein the enveloping component (30) of high bioresistance, biocompatibility and non-toxicity is platinum, iridium, or an alloy of the two materials.

3. An implantable electrode lead according to claim 1, wherein the core component (31) of low electrical resistance consists of an element from the vanadium group ($5^{th}$ subgroup of the classification of elements) or copper group ($11^{th}$ subgroup of the classification of elements).

4. An implantable electrode lead according to claim 3, wherein the core component (31) of low electrical resistance is tantalum, niobium or gold.

5. An implantable electrode lead according to claim 1, wherein the thickness ratio between the bioresistant, biocompatible and non-toxic enveloping component (30) and the core component (31) of low electrical resistance is 1:3 to 1:40.

6. An implantable electrode lead according to claim 1, wherein the thickness ratio in an axial direction of the electrode (1) between the bioresistant, biocompatible and non-toxic enveloping component (30) and the core component (31) of low electrical resistance is between 1:20 and 1:40, preferably between 1:25 and 1:30, most preferably between 1:27 and 1:29.

7. An implantable electrode lead according to claim 1, wherein the ratio in a radial direction of the electrode (1) between the bioresistant, biocompatible and non-toxic enveloping component (30) and the core component (31) of low electrical resistance is between 1:2 and 1:10, and preferably between 1:3 and 1:8.

8. An implantable electrode lead according to claim 1, wherein the electrically active implantable device is one of a pacemaker and cardioverter/defibrillator.

9. An implantable electrode lead according to claim 1, wherein the electrically active regions (5a, 5b) in the distal region deliver one of a stimulation pulse, cardioversion pulse and defibrillation pulse.

10. An implantable electrode lead according to claim 1, wherein the fixation device (6b) in the distal region is one of a passive anchoring and an active anchoring.

11. An implantable electrode lead according to claim 10, wherein the active anchoring (6b) is an electrically active region.

12. An implantable electrode lead according to claim 1, wherein the electrically conductive connection (16) between the proximal connecting unit (4a, 4b, 4c) and the at least one electrically active region is selected from a round wire, a DFT wire, an electrically conductive ribbon, an electrically conductive DFT ribbon, an electrically conductive cable, and an electrically conductive DFT cable.

13. An implantable electrode lead according to claim 1, wherein the electrode body (3) consists of an inner (18) and an outer layer (17) of biostable synthetic material.

14. An implantable electrode lead according to claim 13, wherein the outer layer (17) is a silicone rubber.

15. An implantable electrode lead according to claim 13, wherein the inner layer (18) is composed of polyurethane.

16. An implantable electrode lead according to claim 1, wherein the electrically active regions (5a, 5b) in the distal region are embedded in the outer surface.

* * * * *

UNITED STATES PATENT AND TRADEMARK OFFICE
CERTIFICATE OF CORRECTION

| | | |
|---|---|---|
| PATENT NO. | : 7,617,004 B2 | Page 1 of 1 |
| APPLICATION NO. | : 11/241982 | |
| DATED | : November 10, 2009 | |
| INVENTOR(S) | : Bartels et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 526 days Delete the phrase "by 526 days" and insert -- by 928 days --

Signed and Sealed this

Eighteenth Day of May, 2010

David J. Kappos
*Director of the United States Patent and Trademark Office*